(12) United States Patent  
Moriyama

(10) Patent No.: US 6,281,177 B1  
(45) Date of Patent: Aug. 28, 2001

(54) BATH JELLY AND METHOD OF USING THE SAME

(76) Inventor: Masayasu Moriyama, 2-3-18 Nakayamate-Dori, Chuo-ku, Kobe (JP)

( * ) Notice: Subject to any disclaimer, the term of this patent is extended or adjusted under 35 U.S.C. 154(b) by 0 days.

(21) Appl. No.: 09/502,958

(22) Filed: Feb. 11, 2000

(51) Int. Cl.[7] ............................... C17D 3/20; A61K 7/50
(52) U.S. Cl. ......................... 510/130; 510/158; 510/477; 510/488
(58) Field of Search ...................... 510/130, 158, 510/477, 488; 424/401

(56) References Cited

U.S. PATENT DOCUMENTS

| 5,932,235 | * | 8/1999 | Ninomiya et al. | 424/401 |
| 6,033,680 | * | 3/2000 | Dixon et al. | 424/401 |
| 6,066,608 | * | 5/2000 | Glenn, Jr. | 510/159 |
| 6,080,708 | * | 6/2000 | Glenn, Jr. | 510/130 |

* cited by examiner

Primary Examiner—Necholus Ogden  
(74) Attorney, Agent, or Firm—Ingrid M. McTaggart

(57) ABSTRACT

A bath jelly for creating a gelatinous mixture in a bathtub comprises two components. The first component comprises a powder which when added to hot water produces a gelatinous mixture. The first component typically is a mixture of sodium polyacrylate, ascorbic acid, black tea extract, L-menthol, coloring, and fragrance. The second component comprises a powder which when added to the gelatinous mixture dissolves the mixture and allows the contents of the tub to be easily drained. The second component typically comprises sodium chloride. The gelatinous mixture deep cleans skin by removing sweat and toxins from lower skin layers during bathing.

20 Claims, 5 Drawing Sheets

PRESSURIZED WATER PICKUP

ESTHE JELLY HAS HIGH WATER PICKUP ABILITY.

PRESSURIZED WATER PICKUP

HYGROSCOPICITY MOISTURE ABSORPTION
ESTHE JELLY ABSORBS MOISTURE VAPOR.

GEL INTENSITY
THIS GRAPH SHOWS GEL INTENSITY
THIS GEL INTENSITY IS CHARACTERISTIC OF ESTHE JELLY.

STABILITY
WHILE KEEPING THE TEMPERATURE, ESTHE JELLY CAN KEEP WATER PICKUP ABILITY.

BATH JELLY AND METHOD OF USING THE SAME

TECHNICAL FIELD

The present invention relates to a bath jelly and a method of using the same, and more particularly, to a bath jelly which is prepared in a bathtub by a bather and which is dissolved in the bathtub after bathing by the addition of a dissolving agent.

BACKGROUND OF THE INVENTION

Since the times of Roman baths, bathing has been a luxurious and relaxing experience. Taking a steaming bath has known physiological and psychological benefits such as lowering blood pressure, relaxing muscles, relieving aches and pains and calming the mind. Bathing also cleans the outer layer of the skin by removing surface dirt and oils.

Many bath products are currently available to enhance the bathing experience. For example, bathing salts may be added to a tub of bath water to add a pleasant aroma to the bath and/or to soften the bath water. Bubble bath may be added to a tub of water to create a foam on the water surface and to add a pleasant aroma to the bath water. There are also numerous scented oils and soaps available for use while bathing. In addition, loofas, sponges and pumice stones may also be used to help during bathing to clean the outer layer of the skin.

In contrast to these soothing bath products, to clean below the uppermost surface of the skin, harsh chemicals are generally used. For example, undiluted cold astringents are typically applied to the outer most facial skin layer with cotton swabs whereupon the skin is immediately rinsed in a bathroom skin. This technique may result in the deep cleansing of facial pores but is not a cost effective or a pleasant method for deep cleansing of the remainder of a person's body.

Accordingly, there is a need for a product which allows deep cleansing of skin pores but which does not utilize a cold astringent. Moreover, there is a need for a product which allows deep cleansing of skin pores over a person's entire body without requiring the person to endure the uncomfortable temperatures associated with standing by a bathroom sink while dabbing themselves with a cold astringent.

SUMMARY OF THE INVENTION

Accordingly, an object of the present invention is to provide a bath jelly which promotes a luxurious and relaxing bathing experience.

Another object of the present invention is to provide a bath jelly which allows deep cleansing of skin pores over the entire body surface.

Still a further object of the present invention is to provide a bath jelly which allows deep cleansing of skin pores without the use of cold astringents.

Yet another object of the present invention is to provide a bath jelly which allows a bather to prepare the jelly in a bathtub and which allows the bather to dissolve the jelly in the bathtub by the addition of a dissolving agent.

The bath jelly of the present invention comprises two components. The first component comprises a powder which when added to hot water produces a gelatinous mixture. The first component typically is a mixture of sodium polyacrylate, ascorbic acid, black tea extract, L-menthol, coloring, and fragrance. The second component comprises a powder which when added to the gelatinous mixture dissolves the mixture and allows the contents of the tub to be easily drained. The second component typically comprises pure sodium chloride. Other components may be added to the first powder and other salts may be used as the second powder.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION

Figure 1:
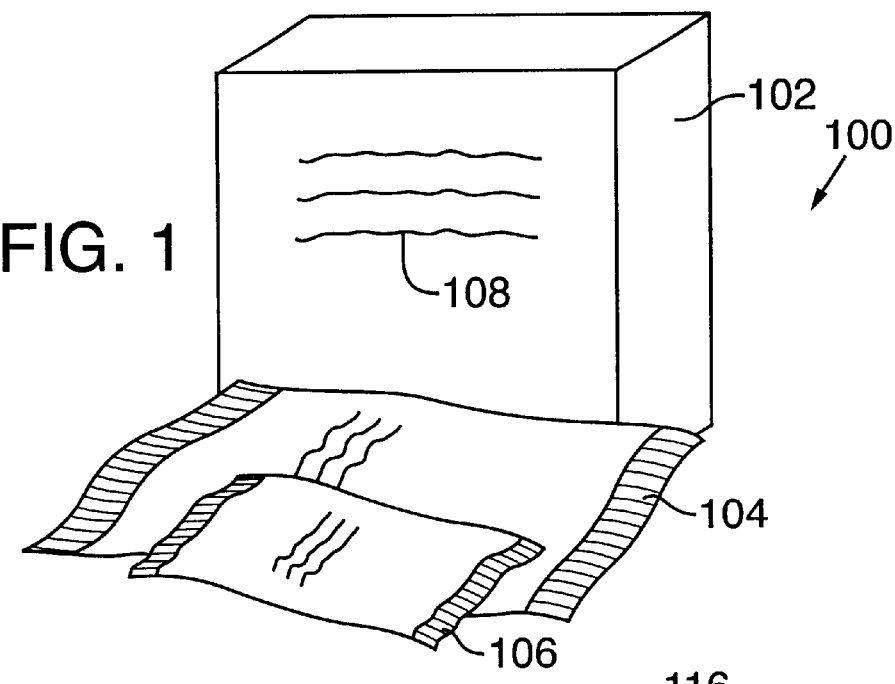
FIG. 1 is a perspective view of the product of the present invention prior to use.

FIG. 1 is a perspective view of the product of the present invention prior to use. In particular, product 100 includes packaging 102, in the form of a cardboard box, and a first foil packet 104 and a second clear packet 106. First foil packet 104 contains a first powder for addition to a bathtub of hot water to form a gelatinous mixture. Second clear packet 106 contains a second powder for addition to the tub of gelatinous mixture to dissolve the mixture into a relatively non-viscous liquid. Instructions 108 typically are printed on the side of packaging 102 and the foil packets 104 and 106, and may also be printed on a separate sheet packaged within box 102.

First foil packet 104 typically includes approximately 190 grams of the first powder and second clear packet 106 typically includes approximately 70 grams of the second powder such that the weight ratio of the first powder to the second powder is approximately 2.7. Other amounts of the powder may be packaged for sale, preferably having the same ratio of approximately 2.7 grams of the first powder for each gram of the second powder. An acceptable range is 2.0 to 3.4 grams of the first powder for each gram of the second powder. Typical package amounts may vary from 95 to 380 grams of the first powder, and 35 to 140 grams of the second powder, respectively. These amounts are sufficient to create the gelatinous mixture in a bathtub full of water for a variety of bathtub sizes.

Figure 2:
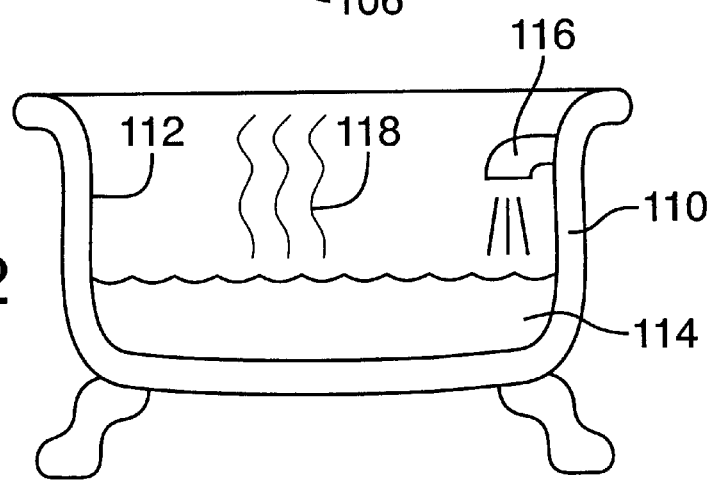
FIG. 2 is a side sectional view of a bathtub filled with hot water.

FIG. 2 is a side sectional view of a bathtub filled with hot water. Bathtub 110 includes an inner tub cavity 112 for holding water 114 therein. In particular, FIG. 2 shows hot water 114 being drawn into tub 110 by a faucet 116. The hot water produces stream 118 and preferably has a temperature of approximately 39 degrees Celsius (103 degrees Fahrenheit). For purposes of the present invention, temperatures in a range of 32 to 47 degrees Celsius (90 to 116 degrees Fahrenheit) will allow the gelatinous mixture to form correctly. If the water is not hot enough, the gelatinous mixture will not form. If the water is too hot, a bather may be scalded. Temperatures of over one hundred and twenty five degrees Fahrenheit typically will scald an adult whereas temperatures above one hundred and sixteen degrees Fahrenheit typically will scald infants, children, and the elderly.

Tub 110 typically is filled with hot water 114 to about one third the capacity of the bathtub, approximately twenty-one gallons, for the addition of the first and second packets as described above. Accordingly, a ratio of twenty-one gallons of hot water is used for approximately one hundred and ninety grams of the first powder. This ratio may also be described as within a range of 0.08 to 0.13 gallons of water per gram of powder. Other amounts of water may be used so long as this water to first powder ratio range is maintained.

Figure 3:
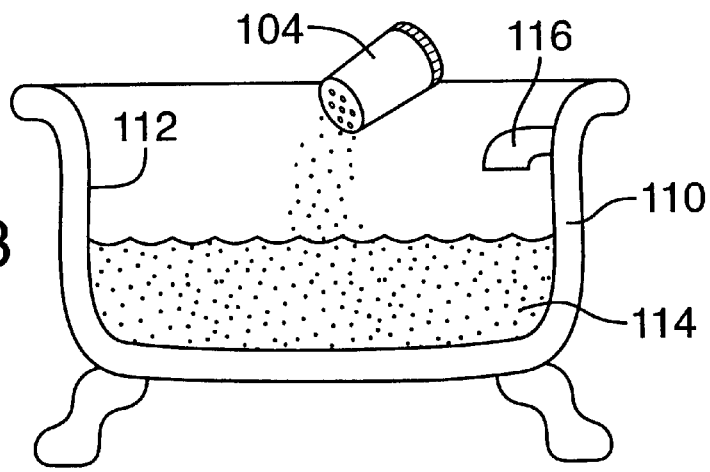
FIG. 3 is a side sectional view of the first powder being added to the bathtub filled with hot water.
Figure 4:
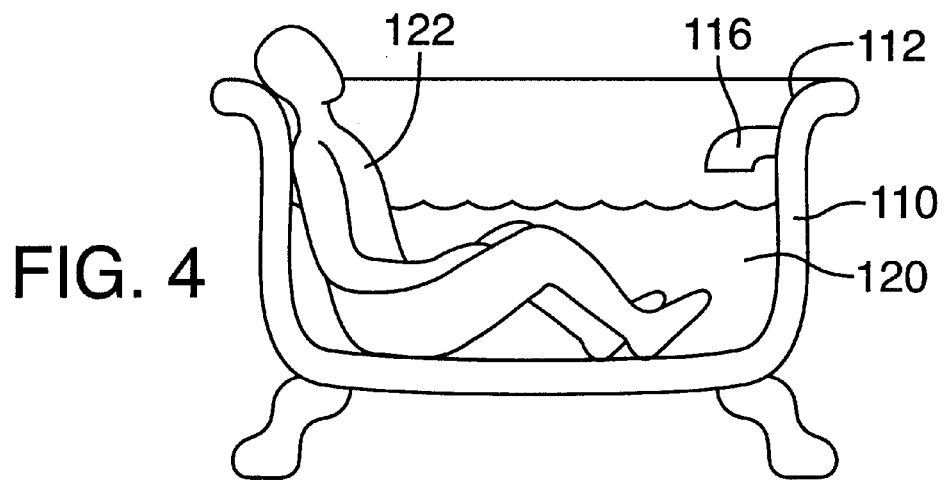
FIG. 4 is a side sectional view of a bather seated in the bathtub filled with the gelatinous mixture.

FIG. 3 is a side sectional view of the first powder being added to the bathtub filled with hot water 114. The contents of the first packet of powder 104 are added to tub 110 filled with hot water 114, as soon as the tub reaches twenty-one gallons of hot water. The powder/water mixture is then gently stirred to facilitate even mixing of the powder throughout the hot water. After approximately five minutes the hot water/powder mixture will have become a gelatinous mixture 120 (FIG. 4). Slightly longer time periods may be required for larger tubs of water to become gelatinous. Similarly, slightly shorter time periods may be required for smaller tubs of water to become gelatinous. At this point gelatinous mixture 120 is ready for bathing.

FIG. 4 is a side sectional view of a bather seated in the bathtub filled with the gelatinous mixture. When the gelatinous mixture is ready for bathing, a bather 122 enters tub 110 and substantially or at least partially submerges themselves in gelatinous mixture 120. The gelatinous mixture typically is slippery so that the bather should be cautious in entering the bathtub. Once the bather is seated in the bathtub the level of the gelatinous mixtures rises due to the volume of the person within the tub. Accordingly, once the bather is substantially submerged in the tub the gelatinous mixture substantially covers the skin of the bather. The mixture should not cover or extend over the bather's head or facial area.

The bather typically will remain substantially or partially submerged in gelatinous mixture 120 for approximately fifteen to twenty minutes. During the time the bather is soaking in tub 110, the gelatinous mixture removes water, sweat and toxins from below the uppermost surface layers of the bather's skin, as will be described more fully below. Accordingly, if the bather remains in the tub for a period of time longer than twenty minutes, it is recommended that the bather drink eight ounces of water. After the bather has soaked for the desired amount of time, bather 122 exits the bathtub. The gelatinous mixture is still slippery at this point and care should be taken in exiting the bathtub.

Figure 5:
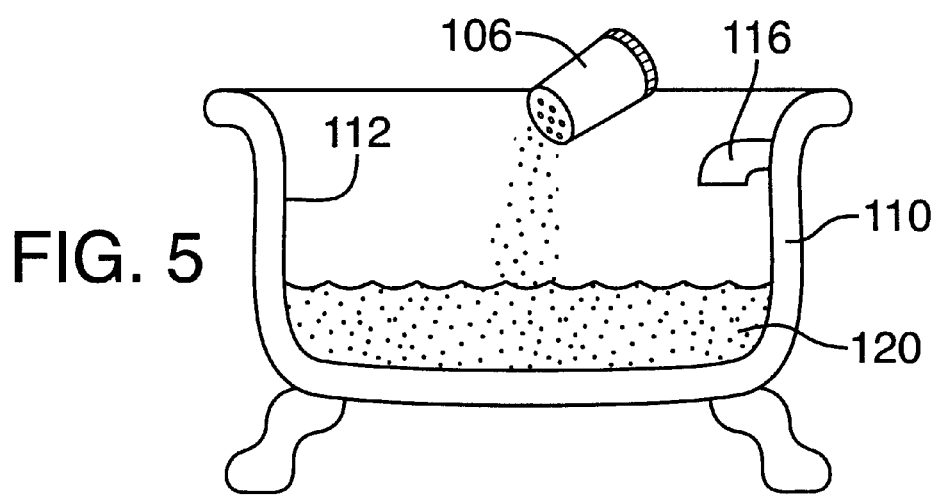
FIG. 5 is a side sectional view of the second powder being added to the bathtub filled with the gelatinous mixture.
Figure 6:
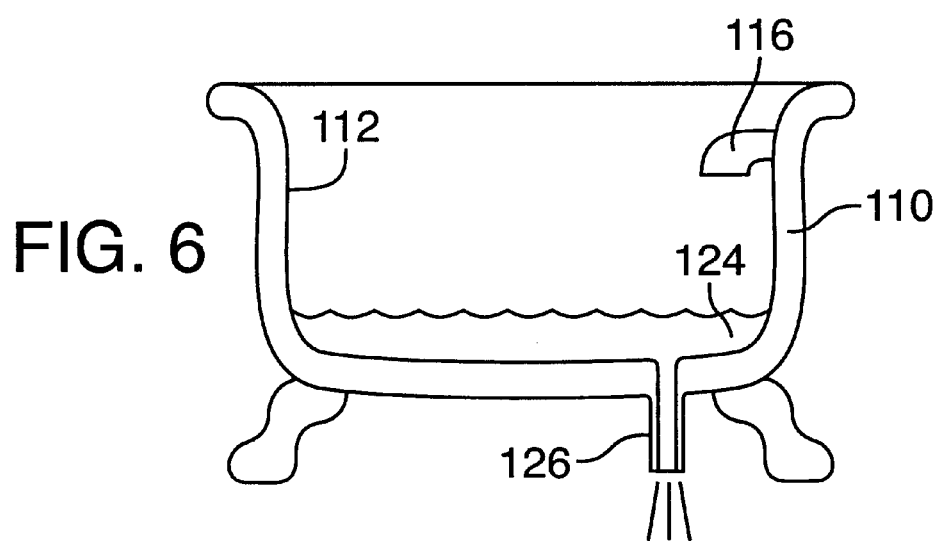
FIG. 6 is a side sectional view of the low-viscosity liquid in the bathtub being drained therefrom.

FIG. 5 is a side sectional view of the second powder being added to the bathtub filled with the gelatinous mixture. After bather 122 has exited tub 110, the bather adds the powder contents of second clear packet 106 to gelatinous mixture 120. Accordingly, approximately seventy grams of the second powder are added to approximately twenty-one gallons of gelatinous mixture 120. The powder/jelly mixture is then gently stirred to facilitate even mixing of the second powder throughout the gelatin. After approximately fifteen to twenty minutes the gelatin/powder mixture will have become a relatively non-viscous liquid 124 (FIG. 6). The second powder, therefore, may be referred to as a dissolving agent or a dissolution agent. Slightly longer time periods may be required for larger tubs of gelatin to become low-viscous liquid. Similarly, slightly shorter time periods may be required for smaller tubs of gelatin to become low-viscous liquid. At this point, the relatively non-viscous liquid may be easily drained from tub 110.

FIG. 6 is a side sectional view of the low-viscosity liquid in the bathtub being drained therefrom. Once the gelatinous mixture has transformed to relatively non-viscous liquid 124, having a viscosity very similar to that of water, the liquid may be drained from tub 110 through a bath drain 126. A small amount of warm or hot water may be added to low-viscous liquid 124 to further decrease its viscosity and/or to facilitate draining of liquid 124. After draining of the tub, the tub should be washed with warm water to remove any remaining liquid 124 or gelatin 120.

As will be understood by those skilled in the art, product 100 should only be used externally and should only be used by adults. The product should not be used by persons with sensitive skin, allergies, open wounds, eczema, or other skin conditions. Typically a small patch of skin should be tested before the bather substantially or partially submerges themselves in the gelatinous mixture. If any adverse skin reaction occurs, a physician should be consulted immediately. The product should not be used in hot tubs, whirlpool baths, or tubs with jets. The product should not be used with other bathing products such as bathing salts or bubble bath. These other bathing products may disturb the chemistry of the present invention thereby prohibiting formation of the gelatinous mixture. Failure to add the second powder to the gelatinous mixture before draining may result in a clogged drain.

The chemical composition of the product will now be described. The first powder of the present invention in a preferred embodiment comprises 75.0% by weight sodium polyacrylate, 16.0% by weight ascorbic acid, 4.9% by weight black tea extract, 0.1% by weight L-menthol, 2.0% by weight coloring or dyes, such as blue, red, orange, or yellow, and 2.0% by weight of fragrance. The sodium polyacrylate may be present in amounts from 50.0 to 95.0%, the ascorbic acid may be present in amounts from 5.0 to 30.0%, the L-menthol may be present in amounts from 0.001% to 2.0%, and the dyes, black tea extract and fragrance may be present in any desired amounts. Moreover, the dyes, black tea extract and fragrance may be eliminated completely.

The second powder preferably comprises pure sodium chloride but other salts may also be used. The second powder may also comprise at least ninety percent by weight sodium chloride with small amounts of other salts added thereto.

Figure 7:
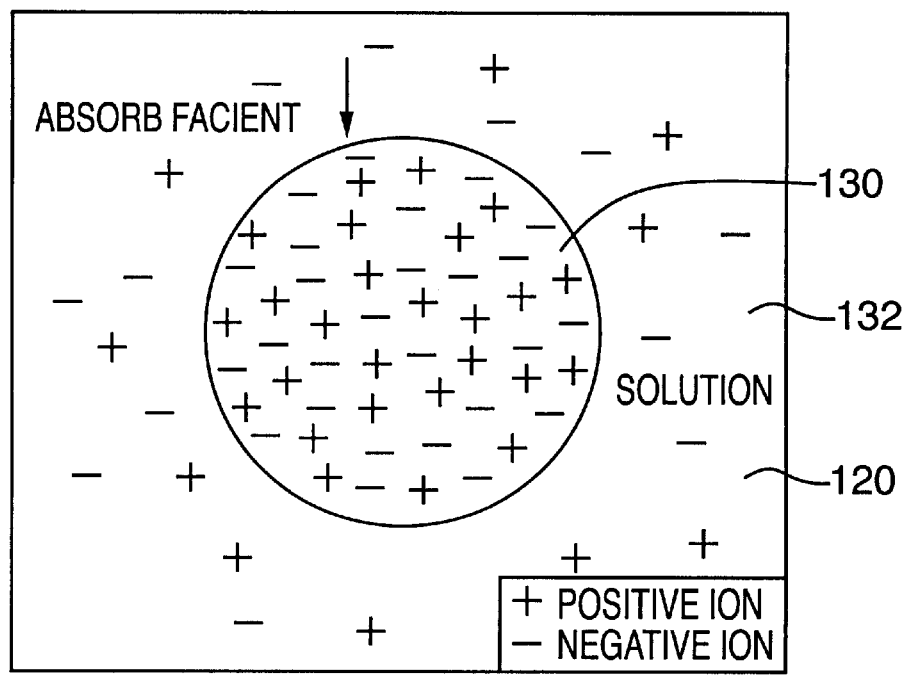
FIG. 7 is a schematic diagram of the water pickup reaction that takes place in the gelatinous mixture.

FIG. 7 is a schematic diagram of the water pickup reaction that is believed to take place in the gelatinous mixture. The product of the present invention is believed to function to remove toxins from deep layers of the skin by removing water which is believed to have toxins complexed therewith. In particular, the water removed from the deep layers of the skin typically is in the form of sweat which may include toxins therein.

A typical water absorption phenomenon is the absorption of water by cotton, pulp or a sponge. These materials absorb water by capillary action and release the water under pressure. In other words, a sponge placed on a plate of water will draw the water upwardly into the sponge. When the sponge is squeezed, the sponge will release the water. In contrast, the product of the present invention absorbs water within molecules and between the chains of molecules in a solution so that the water is not released by the molecule when subjected to pressure. Accordingly, the product of the present invention has a high ability to absorb and retain water regardless of the pressure of the solution.

The ability of the gelatinous mixture to absorb water complexed with toxins is shown by Equation 1:

$$\text{Equation 1:} \quad \text{Amount of Water Pickup} = \frac{K(\text{Penetration})^2(\text{Affinity})}{(\text{Elastic Gum})}$$

wherein K is a constant, the Penetration is a measure of the difference of an ion concentration of a solution with an ion concentration of molecules in the solution, the Affinity is the affinity of the ions in solution for drawing water and toxins from the solution into the molecule, and the Elastic Gum is the construction density of the molecule. In other words, the amount of water (and toxins therein) picked up by the solution is proportional to the square of the Penetration, is proportional to the Affinity, and is inversely proportional to the Elastic Gum. When the Penetration and the Affinity variables are high, and the Elastic Gum variable is low, a large amount of water may be picked up the gelatinous mixture of the present invention.

Still referring to FIG. 7, the Penetration variable is illustrated. Gelatinous mixture 120 includes molecules 130 suspended in a solution 132. In particular, mixture 120 comprises polyacrylic acid natrium having high concentrations of the "$COO^-$" ion and the Sodium "$Na^+$" ion in solution. The difference between these ion concentrations in solution 132 and in molecule 130 defines the Penetration of the ions across the molecule border. In particular, the ions in solution are drawn into molecule 130 such that solution 132 draws water from a person's skin to replenish the ions in solution.

In other words, as water is drawn by the ion solution into the molecule, the concentration of water in the solution is decreased. Due to the decreased water concentration in the solution, the solution draws more sweat and toxins from the deep tissue layers of a person's skin during soaking. As these additional water molecules are broken down and drawn into molecules 132 of solution 130, even more water is drawn from the person's skin. The molecules of the present invention have a high capacity of ion penetration such that this process continues so long as the bather remains soaking in gelatinous mixture 120.

Figure 8:
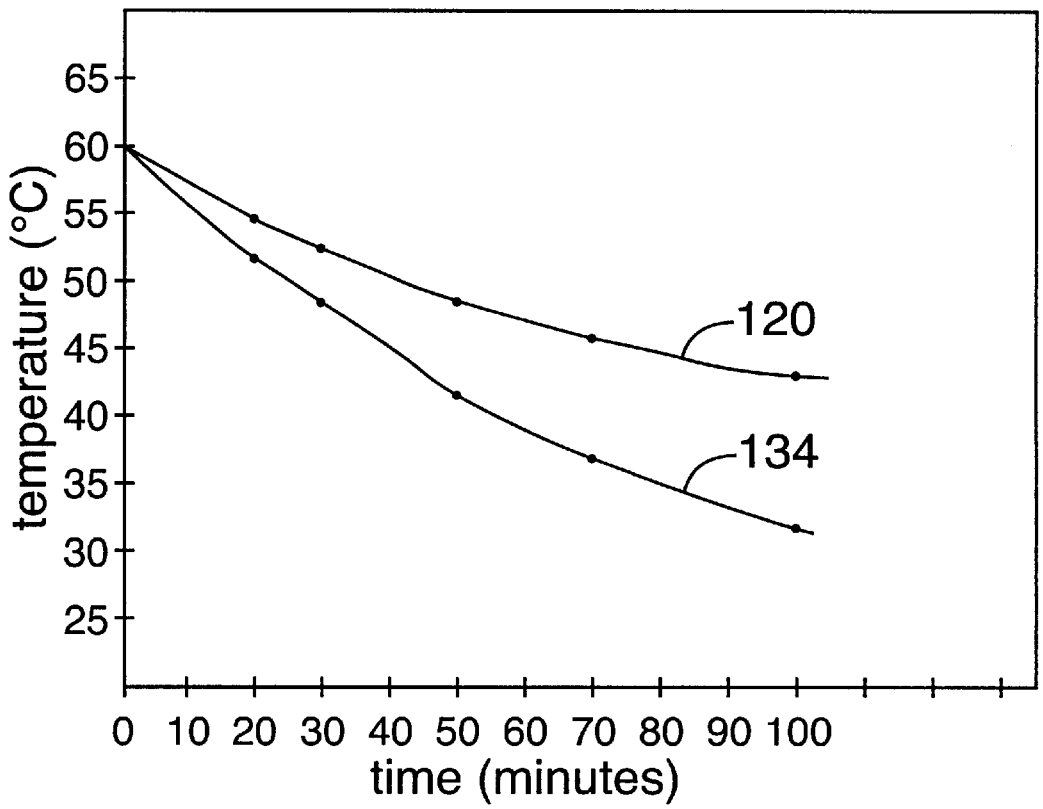
FIG. 8 is a graph illustrating the heat retaining capability of the gelatinous mixture compared to water.

FIG. 8 is a graph illustrating the heat retaining capability of the gelatinous mixture. The graph illustrates the decreasing temperature over time of gelatinous mixture 120 of the present invention compared to a tub of water 134 not having an additive added thereto. In particular, a tub of gelatinous mixture and a tub of water both start at a temperature of sixty degrees Celsius. After approximately sixty minutes, the mixture will have a temperature of approximately fifty degrees whereas the water will have a temperature of approximately forty degrees. Accordingly, not only does the solution of the present invention draw toxins from a bather's skin but the gelatinous mixture tends to remain hotter than regular bath water during a typical bath, further enhancing one's bathing experience. The ability of the gelatinous mixture to retain heat more so than water may be referred to as the mixture having a higher heat retention characteristic than a heat retention characteristic of the water.

Figure 9:
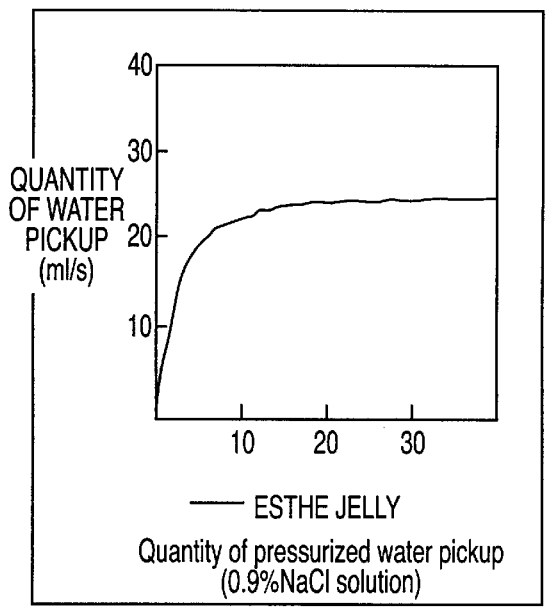
FIG. 9 is a graph showing the quantity of water pickup of the gelatinous mixture while under pressure.

FIG. 9 is a graph showing the quantity of water pickup of the gelatinous mixture. The graph illustrates that the amount of water drawn from solution under pressurized conditions. In particular, the amount of water drawn from solution (in milliliters per gram) increases dramatically during the first ten minutes of soaking. After approximately 20 minutes, the molecules of the present invention tend to become saturated so that only minor additional water removal is achieved under these pressurized conditions. In particular, the gelatinous mixture, under pressurized conditions, picks up approximately 22 milliliters of water per gram of powder added to the amount of water within the water container, within the first ten minutes of the powder being added.

Figure 10:
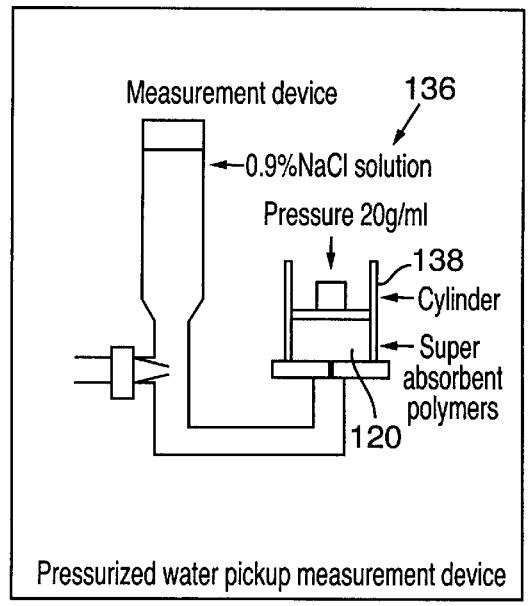
FIG. 10 is a schematic diagram showing the measurement device used to measure the pressurized water pickup of the gelatinous mixture.

FIG. 10 is a schematic diagram showing the measurement device used to measure the water pickup of the gelatinous mixture. In particular, device 136 comprises a pressure cylinder 138 used to pressurize a mixture 120 of the present invention. The test is conducted on the solution at a pressure of twenty grams of pressure per milliliter of mixture.

Figure 11:
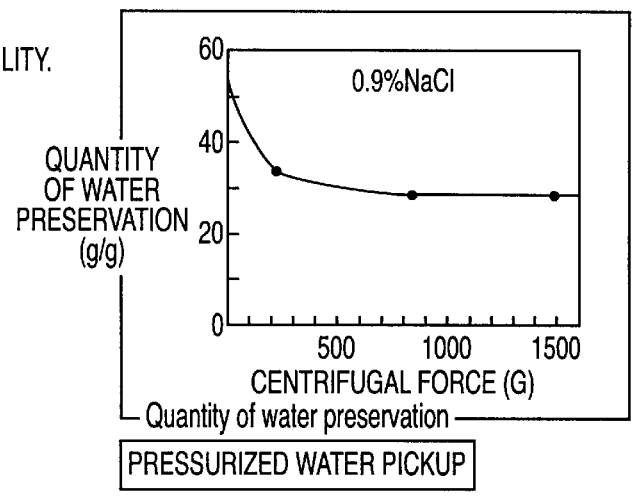
FIG. 11 is a graph showing the quantity of water preservation of the gelatinous mixture while under pressure.

FIG. 11 is a graph showing the quantity of water preservation of the gelatinous mixture while under pressure. The graph illustrates that the mixture of the present invention has a high water retention rate even upon the application of a force. In particular, at a force of zero the mixture retains approximately 53 grams of water per gram of powder added to the solution. At a centrifugal force (G) of approximately 500 the solution retains approximately 30 grams of water per gram of powder added to the solution. The amount of water retention, or preservation, remains approximately constant upon the application of additional force to the mixture.

Figure 12:
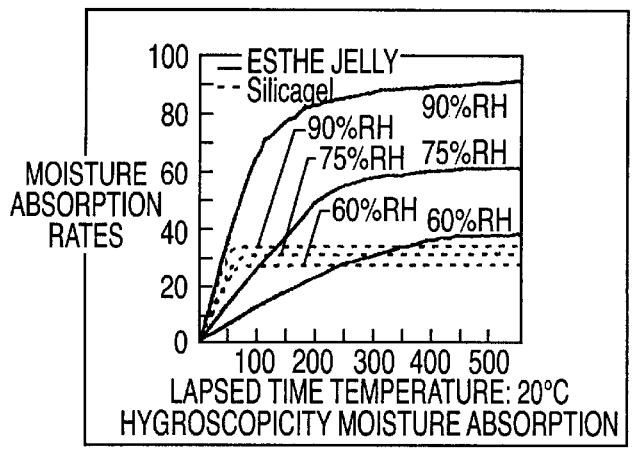
FIG. 12 is a graph showing the water absorption rates of the gelatinous mixture under a variety of conditions.

FIG. 12 is a graph showing water absorption rates of the gelatinous mixture. The graph shows the moisture absorption rate versus time of the gelatin under a variety of conditions, in a non-pressurized, ambient state. In particular, at conditions of ninety percent relative humidity, approximately eighty milliliters of water per gram of powder is absorbed after approximately two hundred seconds. Approximately forty grams of water and approximately twenty grams of water, respectively, are absorbed after two hundred seconds under conditions of seventy-five percent and sixty percent relative humidity, respectively. Accordingly, in each of the relative humidity conditions shown, the product of the present invention has a higher moisture absorption rate than silica gel (the rates for the silica gel are shown in dash lines).

Figure 13:
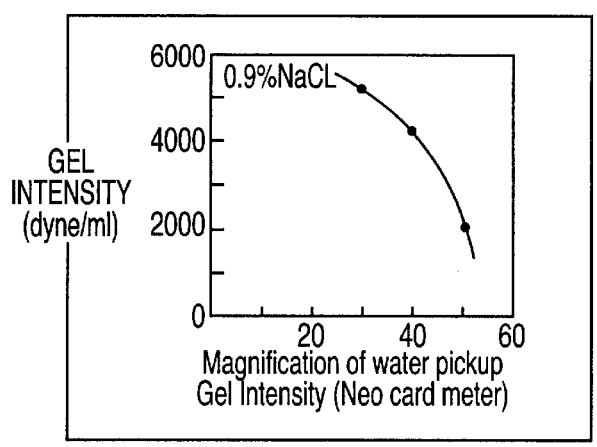
FIG. 13 is a graph showing the intensity of the gelatinous mixture.

FIG. 13 is a graph showing the intensity of the gelatinous mixture. The graph shows the gelatin intensity in dyne per milliliter versus water pickup in the mixture in milliliter per gram. Accordingly, as the force is decreased, the magnification of water pickup increases.

Figure 14:
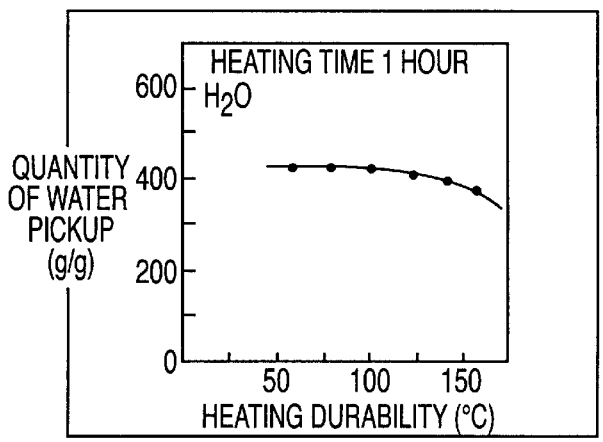
FIG. 14 is a graph showing the stability of the gelatinous mixture.

FIG. 14 is a graph showing the stability of the gelatinous mixture. The graph shows the quantity of water pickup of the gelatin versus the temperature of the gelatin. In particular, as the solution is heated above fifty degrees Celsius, the quantity of water pickup remains essentially constant at approximately 400 grams per gram, with only a very slight decrease in water pickup ability. Accordingly, the mixture of the present invention is thought to have high stability.

While preferred embodiments of the present invention have been shown and described, it will be apparent to those skilled in the art that many changes and modifications may be made without departing from the invention in its broader aspects. The appended claims are intended to cover, therefore, all such changes and modifications as fall within the true spirit and scope of the invention.

I claim:

1. A bath jelly product comprising:
   a powder including fifty to ninety-five percent by weight sodium polyacrylate, five to thirty percent by weight ascorbic acid and 0.001 to two percent by weight L-menthol,
   wherein when said powder is added to a sufficient amount of water the powder and the water will form a gelatinous mixture suitable for bathing.

2. The bath jelly product of claim 1 wherein said powder includes seventy to eighty percent by weight sodium polyacrylate, twelve to twenty percent by weight ascorbic acid, and 0.05 to one percent by weight L-menthol, and wherein said powder further includes a dye, black tea extract and a fragrance.

3. The bath jelly product of claim 1 further comprising a second powder that when added to said gelatinous mixture will transform said gelatinous mixture to a liquid having a low viscosity such that said liquid having a low viscosity easily flows through a drain.

4. The bath jelly product of claim 1 wherein said product further comprises a sufficient amount of water having a temperature in a range of 32 to 47 degrees Celsius and wherein said sufficient amount of water comprises between 0.08 to 0.13 gallons of water per gram of powder.

5. The bath jelly product of claim 1 wherein said gelatinous mixture has a heat retention characteristic which is greater than a heat retention characteristic of water having no additives contained therein.

6. The bath jelly product of claim 1 wherein said gelatinous mixture picks up at least fifteen milliliters of water per gram of powder added to said sufficient amount of water within ten minutes of said powder being added to said sufficient amount of hot water under a pressure of twenty grams per milliliter.

7. The bath jelly product of claim 3 wherein said second powder comprises sodium chloride and wherein said second powder is added to said gelatinous mixture in a ratio range of between 0.1 to 0.5 gallons of gelatinous mixture per gram of the second powder.

8. The bath jelly product of claim 1 wherein said gelatinous mixture draws water from human skin immersed in said gelatinous mixture.

9. A bath jelly product comprising:
   a first powder including fifty to ninety-five percent by weight sodium polyacrylate, five to thirty percent by weight ascorbic acid and 0.001 to two percent by weight L-menthol, wherein when said first powder is added to a sufficient amount of water the first powder and the water will form a gelatinous mixture suitable for bathing; and
   a second powder that when added to said gelatinous mixture will transform said gelatinous mixture to a liquid having a low viscosity.

10. The bath jelly product of claim 9 wherein said first powder includes seventy to eighty percent by weight sodium polyacrylate, twelve to twenty percent by weight ascorbic acid, and 0.05 to one percent by weight L-menthol, wherein said first powder further includes a dye, black tea extract and a fragrance, and wherein said second powder comprises at least ninety percent by weight sodium chloride.

11. The bath jelly product of claim 9 wherein said second powder is added to said gelatinous mixture in a ratio range of between 0.1 to 0.5 gallons of gelatinous mixture per gram of the second powder.

12. The bath jelly product of claim 9 wherein said first powder is added to water having a temperature in a range of 32 to 47 degrees Celsius and wherein said first powder is added to said water in a ratio range of between 0.08 to 0.13 gallons of water per gram of the first powder.

13. The bath jelly product of claim 9 wherein said gelatinous mixture includes a heat retention characteristic which is greater than a heat retention characteristic of water having no additives therein.

14. The bath jelly product of claim 9 wherein said gelatinous mixture picks up at least 15 milliliters of water per gram of the first powder added to said sufficient amount of water within ten minutes of said first powder being added to said sufficient amount of water.

15. The bath jelly product of claim 9 wherein said gelatinous mixture draws water from human skin immersed in said gelatinous mixture.

16. A method of using a bath jelly comprising the steps of:
   providing a water container having at least ten gallons of water contained therein, said water being in a temperature range of 32 to 47 degrees Celsius;
   adding a powder to said water wherein said powder comprises fifty to ninety-five percent by weight sodium polyacrylate, five to thirty percent by weight ascorbic acid and 0.001 to two percent by weight L-menthol; and
   wherein when said powder is added to said water the powder and the water form a gelatinous mixture suitable for bathing.

17. The method of claim 16 further comprising the step of bathing in said gelatinous mixture for at least ten minutes wherein during bathing said gelatinous mixture draws water from human skin immersed in said gelatinous mixture.

18. The method of claim 16 further comprising the step of adding a second powder to said gelatinous mixture that transforms said gelatinous mixture to a liquid having a low viscosity such that said liquid having a low viscosity easily flows through a drain.

19. The method of claim 18 wherein said powder includes seventy to eighty percent by weight sodium polyacrylate, twelve to twenty percent by weight ascorbic acid, and 0.05 to one percent by weight L-menthol, wherein said powder further includes a dye, black tea extract and a fragrance, wherein said second powder comprises at least ninety percent by weight sodium chloride and wherein said second powder is added to said gelatinous mixture in a ratio range of between 0.1 to 0.5 gallons of gelatinous mixture per gram of the second powder.

20. The method of claim 16 wherein said powder is added to said water in a ratio range of between 0.08 to 0.13 gallons of water per gram of powder, and wherein said gelatinous mixture picks up at least 15 milliliters of water per gram of powder added to said water within ten minutes of said powder being added to said water.

* * * * *